United States Patent
Sanikommu

(10) Patent No.: US 12,188,581 B2
(45) Date of Patent: Jan. 7, 2025

(54) STABLE FLOW REGULATOR ASSEMBLY

(71) Applicant: CareFusion 303, Inc., San Diego, CA (US)

(72) Inventor: Narsi Reddy Sanikommu, Prakasam District (IN)

(73) Assignee: CareFusion 303, Inc., San Diego, CA (US)

( * ) Notice: Subject to any disclaimer, the term of this patent is extended or adjusted under 35 U.S.C. 154(b) by 52 days.

(21) Appl. No.: 17/994,715

(22) Filed: Nov. 28, 2022

(65) Prior Publication Data
US 2024/0175499 A1    May 30, 2024

(51) Int. Cl.
*F16K 7/06* (2006.01)
*A61M 5/168* (2006.01)
*A61M 39/28* (2006.01)

(52) U.S. Cl.
CPC ......... *F16K 7/061* (2013.01); *A61M 5/16813* (2013.01); *A61M 39/284* (2013.01); *F16K 7/06* (2013.01)

(58) Field of Classification Search
CPC .......... F16K 7/06; F16K 7/063; A61M 39/284
USPC ....................................................... 251/8, 9
See application file for complete search history.

(56) References Cited

U.S. PATENT DOCUMENTS

| | | | |
|---|---|---|---|
| 628,391 A * | 7/1899 | Clarke | A61M 39/284 251/9 |
| 3,042,067 A | 7/1962 | Hidding | |
| 3,102,710 A * | 9/1963 | Dresden | A01G 25/16 251/9 |
| 3,167,085 A | 1/1965 | Redmer | |
| 3,584,830 A | 6/1971 | Koehn | |
| 3,840,038 A * | 10/1974 | Smith | F16K 7/06 137/637.1 |
| 4,635,897 A | 1/1987 | Gallant | |
| 4,776,558 A | 10/1988 | Bellini | |
| 8,313,081 B2 | 11/2012 | Adelberg | |
| 2007/0051909 A1* | 3/2007 | Bernstein | F16K 7/065 251/9 |
| 2008/0060706 A1 | 3/2008 | Combs | |
| 2020/0324103 A1 | 10/2020 | Pak et al. | |
| 2021/0077806 A1 | 3/2021 | Park et al. | |

FOREIGN PATENT DOCUMENTS

| | | |
|---|---|---|
| CN | 202123269 U | 1/2012 |
| WO | WO-2011136667 A1 | 11/2011 |

OTHER PUBLICATIONS

International Search Report and Written Opinion for Application No. PCT/US2023/034755, dated Feb. 7, 2024, 17 pages.

* cited by examiner

*Primary Examiner* — Robert K Arundale
(74) *Attorney, Agent, or Firm* — Morgan, Lewis & Bockius LLP

(57) ABSTRACT

A stable flow regulator assembly includes a body having an aperture that received a tube. The assembly also includes a worm gear that extends through, and is rotationally movable relative to, the body. A worm wheel is rotationally positioned within the body and is pivotably moved within the body by engagement with the worm gear. The worm wheel also includes a slot, configured to align with the aperture, through which a tube may be extended, and as the worm wheel is moved within the body, the slot and the aperture are moved out of and into alignment to compress and release compression upon the tube.

18 Claims, 13 Drawing Sheets

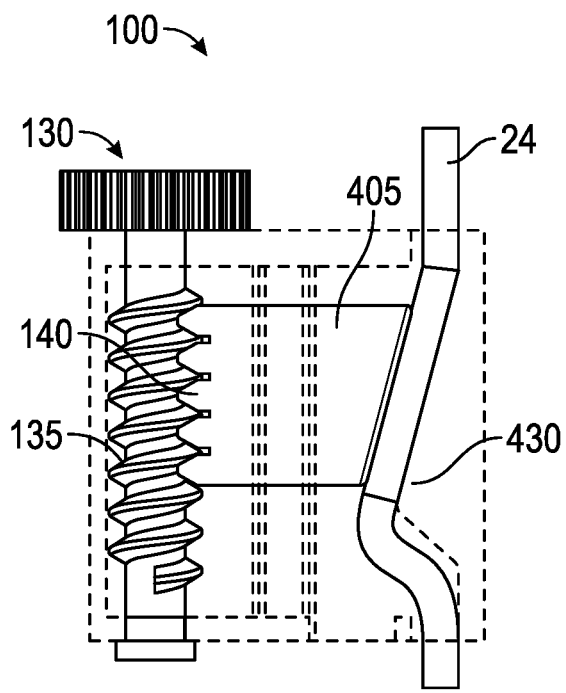
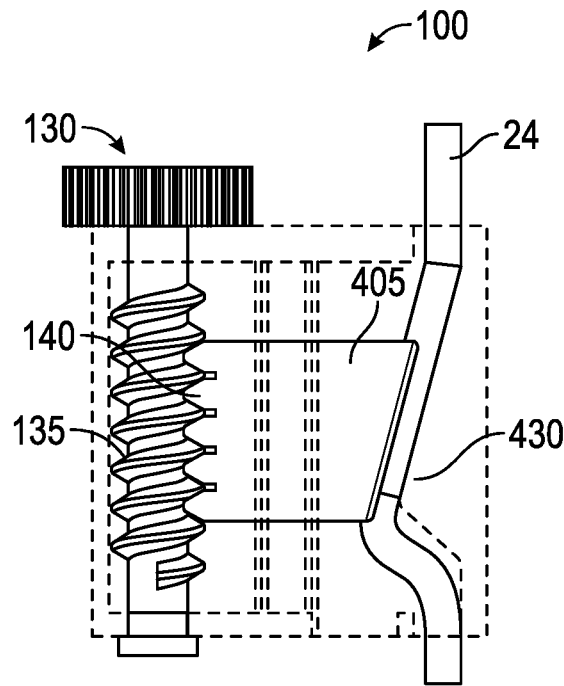
FIG. 13A  FIG. 13B
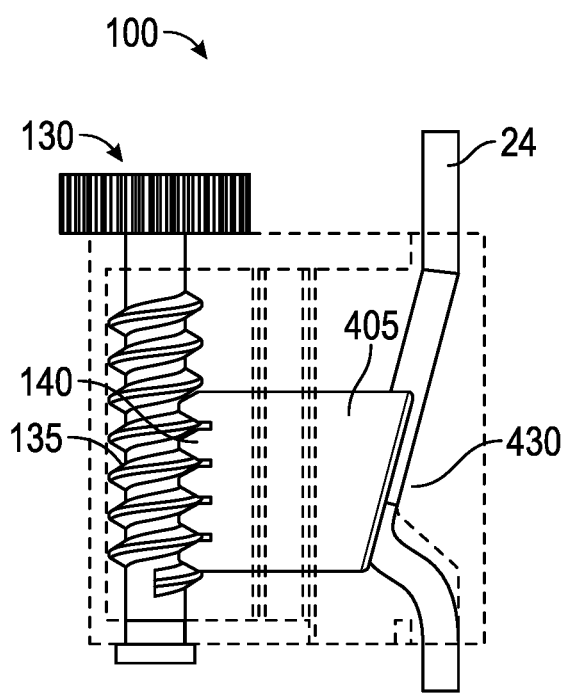
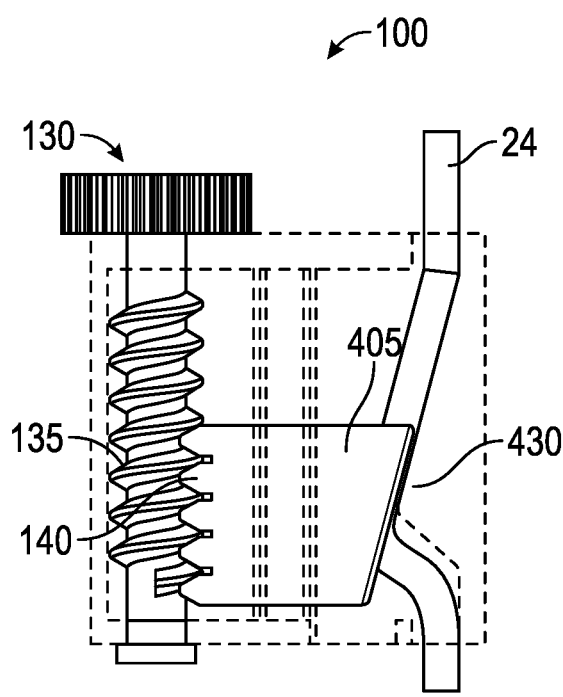
FIG. 13C  FIG. 13D ered in and constitute a part of this specification, illustrate
STABLE FLOW REGULATOR ASSEMBLY

TECHNICAL FIELD

The present disclosure generally relates to a gravity intravenous (IV) set or infusion pump flow control device, and in particular a stable flow regulator assembly.

BACKGROUND

Flow controllers in the form of roller clamps are used in the medical field for intravenous (IV) applications and are typically attached to an IV tube during the manufacturing or assembly process. Such typical roller clamps are then disposed of along with the IV set or the IV tube once the IV application is complete.

Typical roller clamps allow the IV tube to be incrementally occluded by pinching the tubing as the roller clamp is tightened. A typical process is to completely close the roller clamp and regulate the fluid flow rate by rolling the roller clamp upward to open the fluid flow.

SUMMARY

Some roller clamps maintain the roller wheel in position based on a transient fit with the roller body, engagement of tubing with the wheel and friction of the wheel with the roller body. However, over a period at high flow rate with a typical roller clamp, the wheel drifts away from its set position and causes an inaccurate rate of fluid delivery through the tube.

Thus, it is desirable to provide a flow regulator assembly that provides structural stability to control the fluid flow consistently without variation from the adjusted or set flow rate. It is also desirable to provide a flow regulator assembly that can be added to IV tubing as needed in the field, thus eliminating the need to preassemble the flow regulator assembly with a specific IV set or IV tube. In addition, it is desirable to provide a flow regulator assembly that may be reused with different IV sets or IV tubes.

Some embodiments described herein include stable flow regulator assemblies that include a body comprising a first side configured to be coupled to a second side; the first and second sides each comprising respective first and second apertures, the apertures configured to be aligned when the first side is coupled to the second side; a first and second gear mount aligned on an axis; a worm gear comprising a gear thread and configured to be rotationally positioned through the first and second gear mount along the axis; and a worm wheel comprising a rotation axis, worm wheel teeth spaced from the rotation axis, and a tube slot, the worm wheel being configured to be rotationally held within the body, the worm wheel teeth being configured to engage the gear thread, and the tube slot being configured to align with the first and second apertures, wherein rotation of the worm gear translates to rotation of the worm wheel and moves the tube slot relative to the first and second apertures.

In some embodiments, flow regulator assemblies may include a body comprising an enclosed housing having an aperture extending through the body; a worm gear comprising a gear thread and configured to be rotationally positioned through the body; and a worm wheel configured to be rotationally positioned within the enclosed housing and to be moved rotationally by rotation of the worm gear, the worm wheel comprising a tube slot configured to align with the aperture, wherein rotation of the worm gear translates to rotation of the worm wheel within the body and moves the tube slot relative to the first and second apertures.

Certain embodiments described herein are directed to stable flow regulator assemblies including a body comprising an enclosed housing having an aperture extending through the body; a worm gear comprising a first gear thread and a second gear thread extending in a opposite direction as the first gear thread, the worm gear being configured to be rotationally positioned within the enclosed housing; and a worm wheel comprising a first arm and a second arm, the first arm being configured to engage the first gear thread, and the second arm being configured to engage the second gear thread, the worm wheel further comprising a tube slot configured to align with the aperture, wherein rotation of the worm gear in a first direction moves the first and second arm toward each other.

Some embodiments herein describe a stable flow regulator assembly for regulating fluid flow, comprising: a body comprising: a first side configured to be coupled to a second side; a first and second gear mount aligned on an axis between the first side and second side; a tube pathway configured to receive and retain a tube extending through the body; a worm gear comprising a gear thread and configured to be rotationally positioned through the first and second gear mount along the axis; and an actuator configured to be positioned within, and moveable relative to, the body, the actuator comprising teeth configured to engage the gear thread, wherein rotation of the worm gear translates to movement of the actuator within the body to move the actuator from an open configuration, wherein the regulator permits fluid flow, to a closed configuration, wherein the regulator restricts fluid flow. In some embodiments, the first and second sides each comprise respective first and second apertures, the apertures configured to be aligned when the first side is coupled to the second side, wherein the actuator comprises a worm wheel comprising a rotation axis, teeth spaced from the rotation axis, and a tube slot, the worm wheel being configured to be rotationally held within the body, the teeth being configured to engage the gear thread, and the tube slot being configured to align with the first and second apertures, wherein rotation of the worm gear translates to rotation of the worm wheel and moves the tube slot relative to the first and second apertures. In certain embodiments, the actuator comprises a rack configured to be movable along a linear track within the body.

The foregoing and other features, aspects and advantages of the disclosed embodiments will become more apparent from the following detailed description and accompanying drawings.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure.

FIGS. 13A-13D depict partial transparent elevation views of a stable flow regulator assembly in varying stages of operation.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Figure 1:
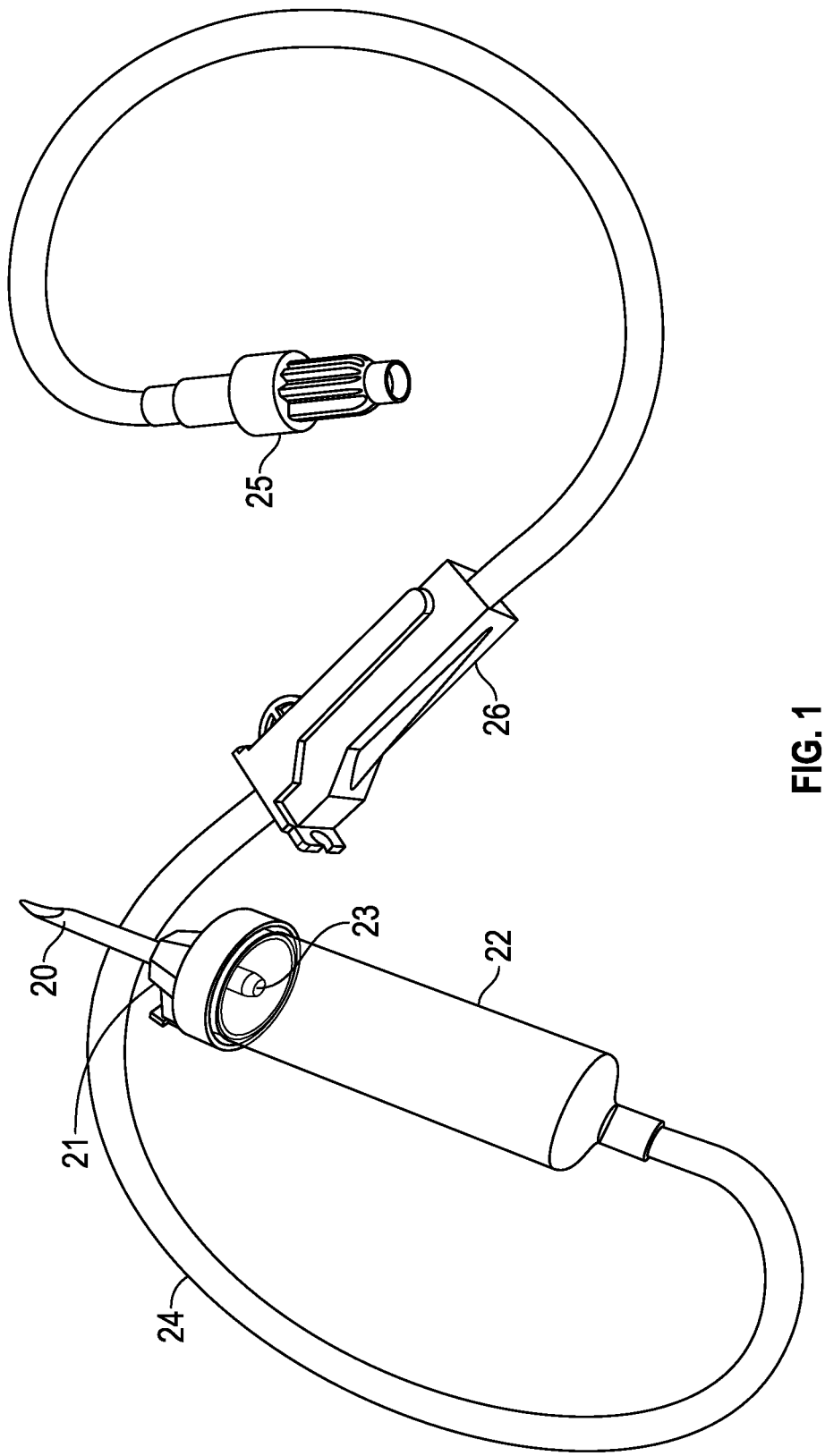
FIG. 1 depicts a perspective view of an example infusion set having a typical roller clamp.

The present disclosure relates to a substitute for a roller clamp and in particular to a roller clamp for use in gravity infusion. A roller clamp regulates the flow rate of a medical fluid (for example a solution of a drug to be administered to a patient, or blood) flowing through a tube. Typically, a standard infusion set is used to infuse the fluid. An example of a standard infusion set is shown in FIG. 1.

The infusion set includes a piercing spike 20 which may either be a sharp spike for piercing rubber stoppers or rounded and blunt for insertion into a bag. The spike contains one channel for fluid and optionally a second channel for venting. A vent 21 is usually present in the vicinity of the piercing spike to allow air to flow into the drip chamber 22. The vent 21 may be provided with a bacterial filter to prevent bacteria from entering the equipment.

The drip chamber 22 has a drip generator 23 at the top of the drip chamber 22 that produces drops of a certain size. Drops from the drip generator 23 fall into the drip chamber 22 such that the drip chamber 22 is partially filled with liquid. This prevents air bubbles from entering the connector tube 24, which would be harmful to a patient. A particle filter may be provided at the lower aperture of the drip chamber 22.

The connector tube 24 connects the drip chamber 22 with the patient. The connector tube 24 is usually around 150 cm long and can be manufactured from PVC. The tube 24 is shown shortened in FIG. 1 for clarity. The connector tube 24 typically has a continuous diameter throughout the length of the tube.

At the end of the connector tube 24 is a Luer fitting 25 which is standardized for connection to all other pieces of apparatus having a standard Luer cone. The person skilled in the art will appreciate that the Luer fitting 25 can be fitted to a hypodermic needle (not shown) for infusing the medical fluid into the circulatory system of a patient (e.g., into a vein).

Between the drip chamber 22 and the Luer fitting 25 and engaging with the connector tube 24, is a roller clamp 26. The present disclosure is concerned with an improved flow regulator assembly, but a typical roller clamp 26 as known in the art will now be described for background information.

Figure 2:
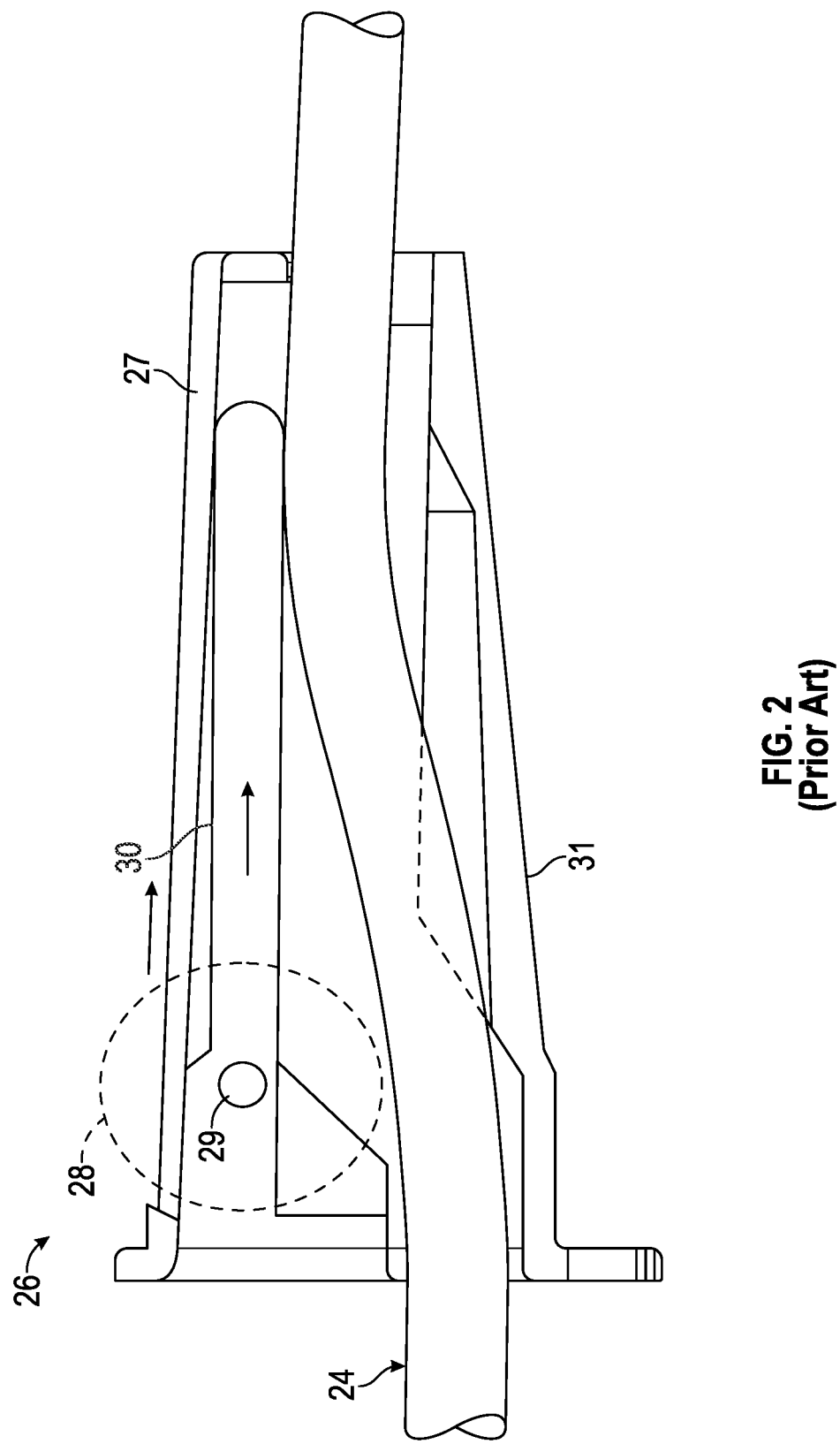
FIG. 2 depicts a cross-section side view of the roller clamp of FIG. 1.

The roller clamp 26 illustrated in FIG. 2 has two opposing side walls 27 having a pair of guide grooves 30 that are aligned with each other and face each other. A flow-regulating roller 28 is provided having axially-projecting shafts 29 protruding from the centers of each side of the roller 28. The roller 28 is shown in outline for clarity. The shafts 29 of the roller 28 are captured by and seated in the guide grooves 30 so that the roller 28 can move up and down the guide grooves 30 as indicated by the arrows in FIG. 2.

The entire roller clamp 26 has four walls (see FIG. 1) in an open-ended boxlike construction and is dimensioned and configured to receive the connector tube 24. In use, the tube 24 passes through the roller clamp 26, between the two opposing side walls 27, the roller 28 and a guide wall 31 that is opposed to the roller 28.

In the roller clamp 26, the surface of the guide wall 31 converges along its length toward the position of the guide grooves 30 in the downward direction of the guide grooves 30 (e.g., in the direction of the arrows in FIG. 2). This tends to urge the connector tube 24 within the roller clamp 26 toward the guide grooves 30 and thus toward roller 28.

Thus, rolling the roller 28 downwardly along the guide grooves 30 in the direction of the gradually closer guide wall 31 in the direction of the arrows causes the roller 28 to impinge against the connector tube 24. As the roller 28 impinges on the tube 24, the tube 24 becomes squeezed, as it is a flexible material such as PVC, and the lumen of the infusion tube 24 therefore becomes smaller. In this way, by narrowing of the lumen, the flow rate of liquid passing through the connector tube 24 can be regulated.

Thus, the roller clamp 26 controls the flow rate through the infusion tube 24 by clamping the infusion tube 24 between the roller 28 and the guide wall 31. This provides for a course flow rate change because a small movement of the roller 28 causes a large change in the flow rate of the fluid through the tube 24. Also, the force of the fluid in the tube 24 exerts a biasing force against the roller 28, which often leads to slippage of the roller 28 (e.g., the roller 28 rolls back) from the adjusted position.

In addition, the roller clamp 26 requires preassembly with the tube 24 when the tube 24 is connected to infusion components such as the drip chamber 22 and the Luer fitting 25, for example. Thus, the roller clamp 26 cannot be added on to an IV set when the tube 24 is already connected to other components. Similarly, since the roller clamp 26 is preassembled as part of an IV set, it is typically disposed of with the IV set and not reused.

In aspects of the disclosure, stable flow regulator assemblies function as tubing clamps for IV tubing and IV sets in place of typical roller clamps. The stable flow regulator assembly described herein provides full clamping (e.g., no flow) for a wide range of tubing sizes, provides the ability to apply and release clamping pressure by rotating a dial and provides the ability to gradually adjust the clamping pressure to provide for a target flow rate. The stable flow regulator assembly also provides for maintaining the target flow rate over time. Thus, once the stable flow regulator assembly is adjusted so that the fluid flow is set to the desired flow rate, the stable flow regulator assembly will maintain that setting for a complete fluid transfer process unless specifically adjusted to a different flow rate.

Figure 3:
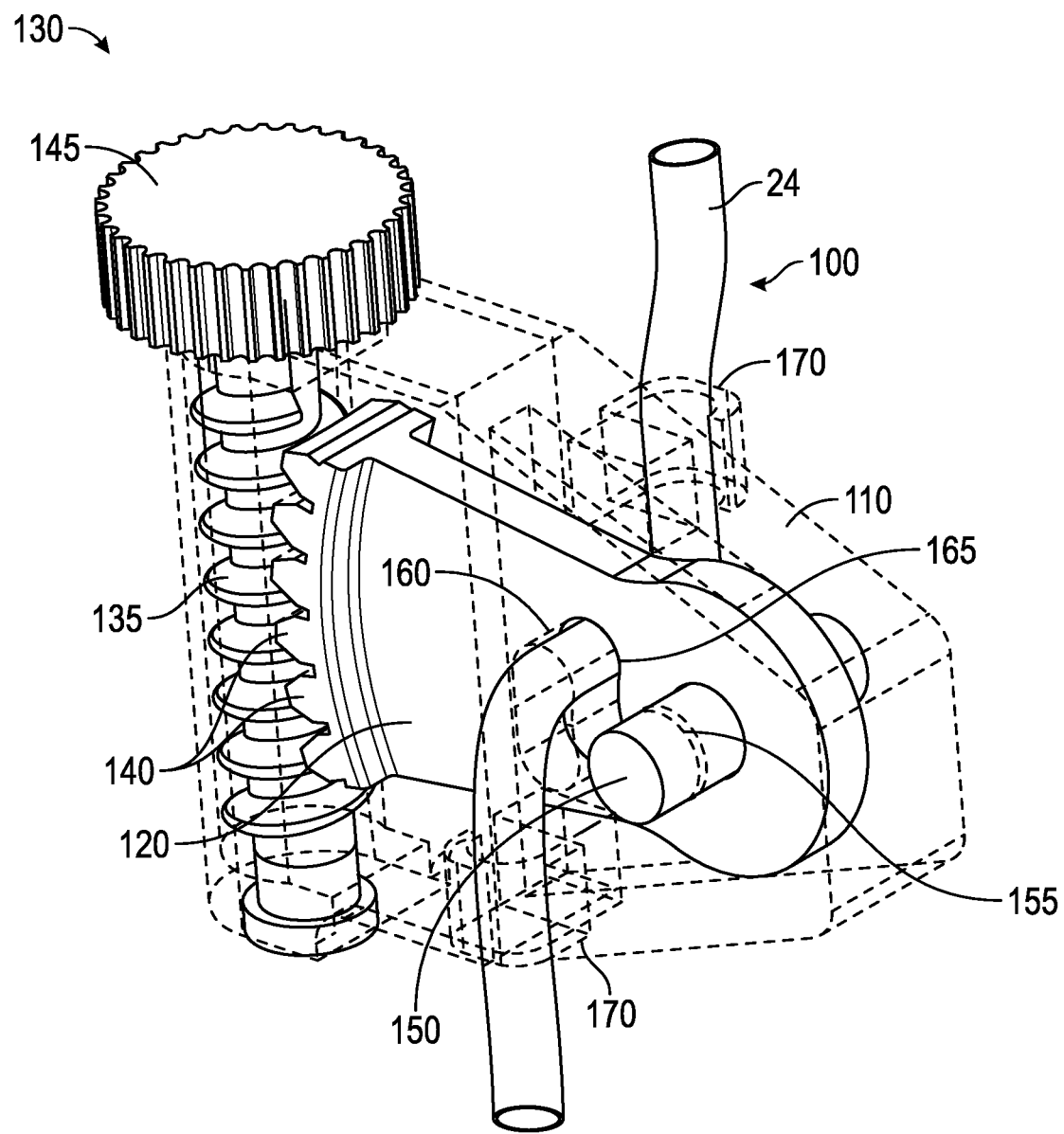
FIG. 3 depicts a perspective view of a stable flow regulator assembly described in connection with embodiments disclosed herein.

With reference to FIGS. 3-7D, embodiments of a stable flow regulator assembly 100 are shown. The stable flow regulator assembly 100 has a body 110 having a semi-rigid or rigid construction (e.g., hard plastic) and is dimensioned and configured to receive tubing, such as connector tube 24. The body 110 is sized to house a worm wheel 120 that is pivotably positioned within the body 110. The body 110 is also configured to couple to a worm gear 130. As depicted in FIG. 3, the worm gear 130 includes a worm thread 135 that is configured to engage gears or teeth 140 on the worm wheel 120. The worm gear 130 includes a worm gear dial 145 that extends outside of the body 110. Although the body 110 is shown in some aspects of the present disclosure, such as FIGS. 3, 5, 9, 11, and 13A-13D, as being at least partially transparent, it should be understood that the present disclosure contemplates embodiments in which any of the body 110 and/or another portion of the stable flow regulator assembly can be made of a material that is semi or fully transparent, or is opaque.

The worm wheel 120 is rotationally positioned within the body 110 such that as the worm gear dial 145 is rotated, the worm wheel 120 moves between an elevated and a lowered position. As the worm gear dial 145 is rotated in a first angular direction, the worm gear thread 135 rotates and engages the teeth 140 on the worm wheel 120, causing the worm wheel 120 to pivot in a first direction. As the worm gear dial 145 is rotated in a second angular direction, opposite the first angular direction, rotation of the worm gear thread 135 engaging the teeth 140 causes the worm wheel 120 to pivot in a second direction, opposite the first direction. The worm wheel 120 preferably includes a worm wheel rotation shaft 150 that extends through a body shaft aperture 155. The worm wheel 120 pivots within the body 110 about an axis formed by the worm wheel rotation shaft 150.

Body 110 preferably includes the body to passage 160 through which to 24 may extend. The worm wheel 120 also includes a worm wheel to slot 165. When the worm wheel 120 is positioned within the body 110, the body tube passage 160 in the worm wheel tube slot 165 are aligned to permit insertion of the tube 24 through each of the passage 160 and the slot 165. The stable flow regulator assembly 100 can include a tube holder 170 on each side of the body 110 to help manage tube 24 control during operation.

Figure 4:
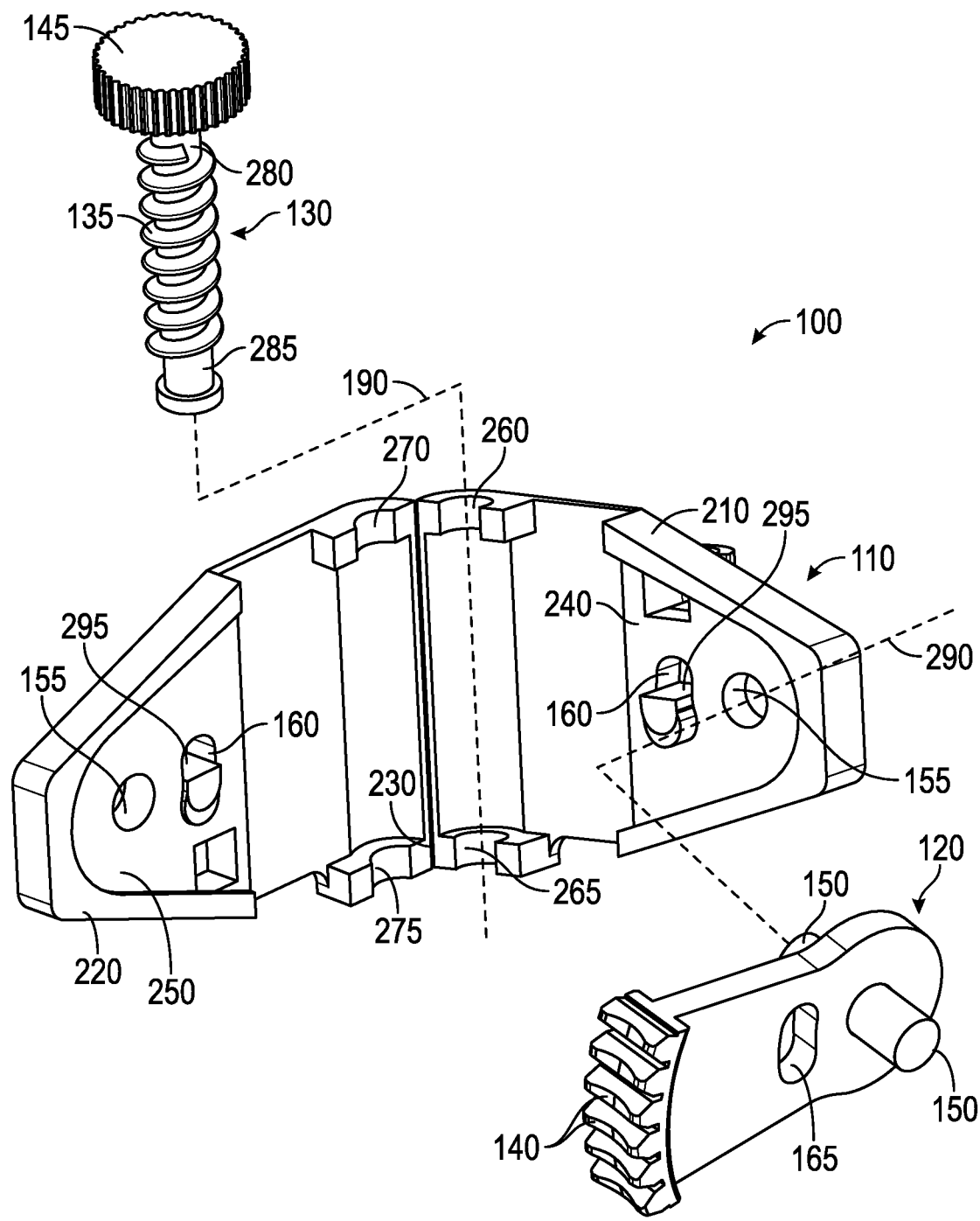
FIG. 4 depicts an exploded view of a stable flow regulator assembly described herein.

FIG. 4 illustrates an exploded view of the stable flow regulator assembly 100 depicting the worm gear 130, the body 110, and the worm wheel 120 as three separate pieces. In some embodiments, the body 110 can be comprised of two separate pieces, a body first part 210 and a body second part 220 that are coupled together to form the body 110. In some embodiments, the body first part 210 in the body second part 220 can be attached by a living hinge 230, and in other embodiments, the body first and second parts 210, 220 can be separate pieces. The first part 210 and the second part 220 preferably attached to each other through snap fit mechanisms, or the parts 210, 220 can be coupled by an adhesive, ultrasonic bonding, or other manufacturing processes.

The first part 210 includes a first part internal face 240 that engages or faces a second part internal face 250 of the second part 220. The first part internal face 240 preferably defines worm gear mounts 260, 265, which are illustrated as two semi-cylindrical channels along the living hinge 230 of the first part 210. The second part internal face 250 preferably defines worm gear mounts 270, 275, also illustrated as two semicylindrical channels along the living hinge 230 on the second part 220. When the first and second parts 210, 220 are coupled together, worm gear mounts 260, 270 on the respective first and second part 210, 220 form a first cylindrical channel or pathway. Likewise, when the first and second parts 210, 220 are coupled together, worm gear mounts 265, 275 on the respective first and second part 210, 220 form a second cylindrical channel or pathway.

The worm gear 130 preferably includes a first worm gear post segment 280 positioned between the worm gear thread 135 and the worm gear dial 145. The first worm gear post segment 280 consists of a substantially cylindrical segment of the worm gear 130. The worm gear 130 also preferably includes a second worm gear post segment 285 positioned on an opposite side of the worm gear thread 135 than the first worm gear post segment 280. The second worm gear post segment 285 also consists of a substantially cylindrical segment of the worm gear 130.

The first and second worm gear post segments 280, 285 are configured to be received between the body first and second parts 210, 220 and aligned along a worm gear axis 190, with the first and second worm gear posts 280, 285 positioned within the cylindrical channels or pathways created by the worm gear mounts 260, 270 on one side of the body 110 and the worm gear mounts 265, 275 on the other side of the body 110. The worm gear 130 is positioned within the body 110 with the first and second gear worm posts 280, 285 functioning as bearings and allowing the worm gear 130 to freely rotate in clockwise or counterclockwise directions.

As illustrated in FIG. 4, the worm wheel 120 is configured to rotationally or pivotally reside within the body 110 when the body 110 is assembled. The worm wheel 120 pivots about a worm wheel shaft axis 290 that is aligned along the worm wheel rotation shaft 150 when the shaft 150 is inserted through the body shaft aperture 155. As the worm wheel 120 has rotation shafts 150 on both sides of the wheel 120, each of the shafts 150 extends through a respective body shaft aperture 155 in the body 110. When the first and second parts 210, 220 are coupled together, the worm wheel 120 is held in place by the internal structure along the faces 240, 250 and the shafts 150 extending through the apertures 155. As explained with reference to FIG. 3, the dimensions of the body 110, the worm wheel 120, and the worm gear 130, and the dimensions and positions of the respective features described, the teeth 140 of the worm wheel 120 are configured to engaged the worm gear thread 135 such that while the worm gear 130 is rotated, the rotational movement of the thread 135 will move the worm wheel 120 upward or downward depending on the direction of rotation.

As the worm wheel 120 is rotated within the body 110, a cross-sectional passage dimension is changed through the body tube passage 160 in relation to the worm wheel tube slot 165. When a tube 24 extends through the passage 160, the relative change in position of the worm wheel 120 relative to the body 110 will cause the dimension through the passage to change. For example, in one position of the worm wheel 120, the passage 160 and the slot 165 can be aligned, permitting a completely open tube 24, and thereby permitting full flow through the tube 24. As the worm wheel 120 is rotated within and relative to the body 110, the passage 160 and the slot 165 will move to a position where the passage 160 and slot 165 are offset from each other, thereby reducing the dimension through the passage. As the tube 24 extends through the passage 160 and slot 165, the tube 24 will be cinched or clamped down at the interfaces between the worm wheel 120 and the body 110, and the clamping of the tube 24 by the offsetting alignment of the passage 160 and the slot 165 will thereby incrementally restrict flow through the tube 24.

FIG. 4 illustrates that the body tube passage 160 can include a tube passage support 295. As depicted, the support 295 may have a planar surface that is configured to engage the tube 24 extending through the passage 160. In some embodiments, the support 295 may have surfaces of different shapes and configurations to change the degree of clamping provided by the offsetting of the passage 160 and slot 165 during use. The planar surface of the support 295 can provide a flat surface against which the worm wheel 120 and tube slot 165 can press the tube 24 against. In some embodiments, the tube passage support 295 of the first part 210 is configured to extend toward the second part 220 and can have a profile that is aligned with the worm wheel tube slot 165, such that the support 295 extends into the tube slot 165 when the body 110 is coupled together. In some embodiments, the support 295 on the second part 220 is configured to extend toward the first part 210 and can also have a profile that is aligned with the worm wheel tube slot 165, such that the support 295 on the second part 220 extends into the tube slot 165 when the body 110 is coupled together. In some embodiments the passage support 295 is configured to extend entirely through the worm wheel tube slot 165 when the body 110 is coupled together. This configuration provides a more stable and constant platform against which the tube 24 can be pressed when the worm wheel 120 is rotated relative to the body 110. As the passage support 295 in some embodiments has the same or similar profile as the tube slot 165, it does not obstruct the rotation or pivot functionality of the worm wheel 120 within the body 110.

Figure 5:
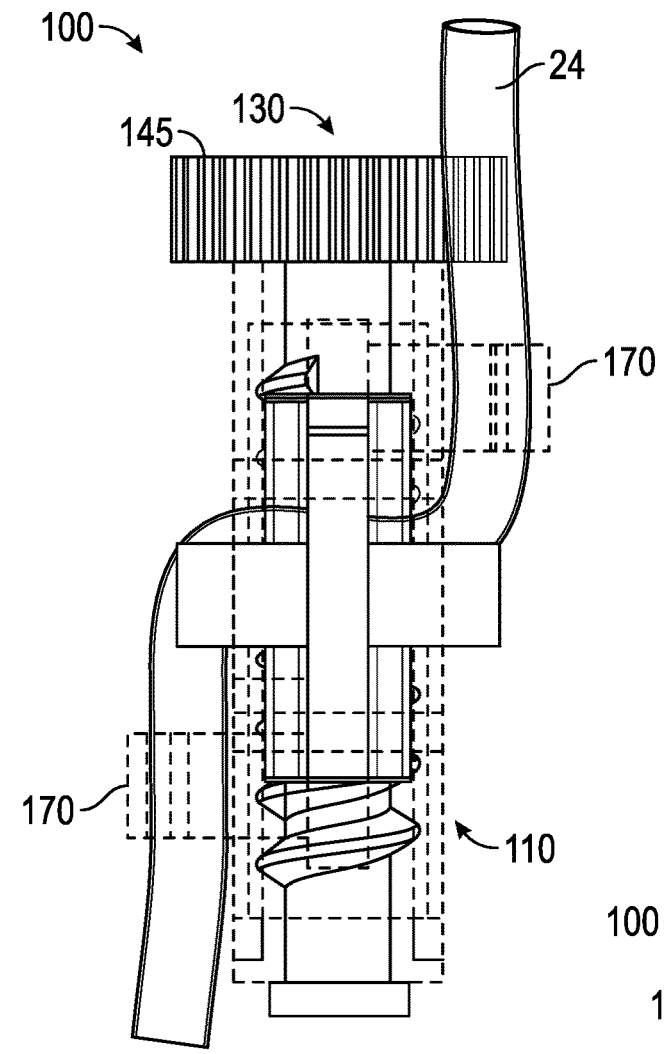
FIG. 5 depicts a partial transparent elevation view of a stable flow regulator assembly described herein.
Figure 6:
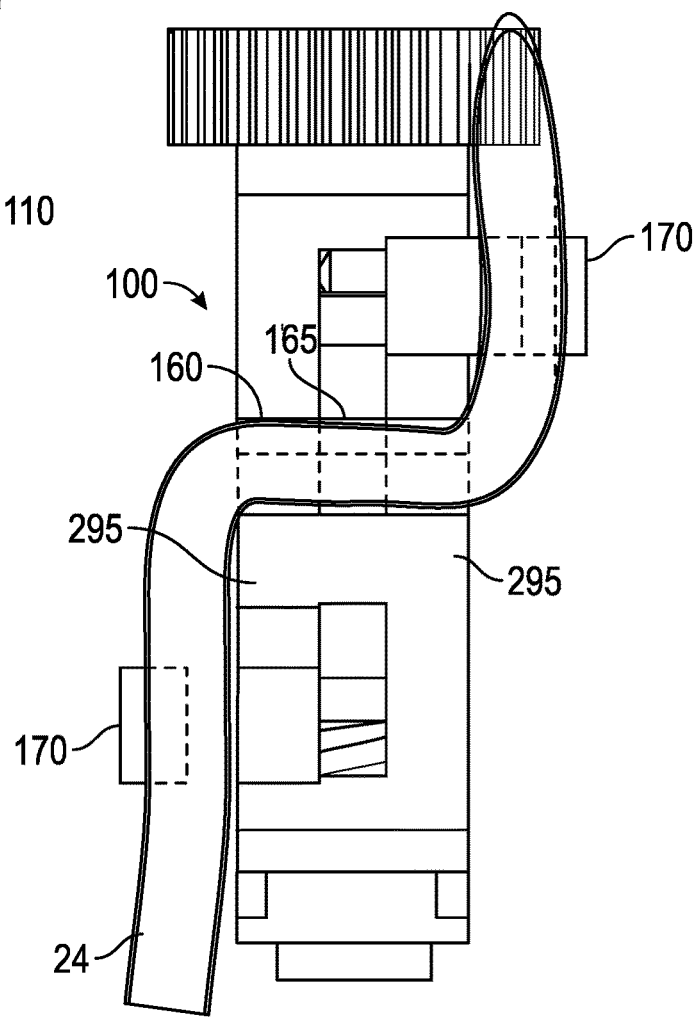
FIG. 6 depicts a partial cross-sectional view of a stable flow regulator assembly described herein.

FIG. 5 illustrates a partial transparent elevation view of the stable flow regulator assembly 100 with a tube 24 extending through the body 110. The tube 24 is illustrated as descending on one side of the body 110, through the body 110, and continuing to extend on an opposite side of the body 110. The tube 24 can be held in placed on each side of the body 110 by tube holders 170. FIG. 6 illustrates a partial cross-sectional view of a stable flow regulator assembly 100 that more clearly depicts the tube 24 traversing the body 110. As illustrated, the tube 24 extends through the body tube passage 160 and the worm wheel tube slot 165 from one side of the body 110 to the other side. The tube 24 extends along the tube passage support 295 and can be held in place on each of the body 110 by tube holders 170.

Figure 7A:
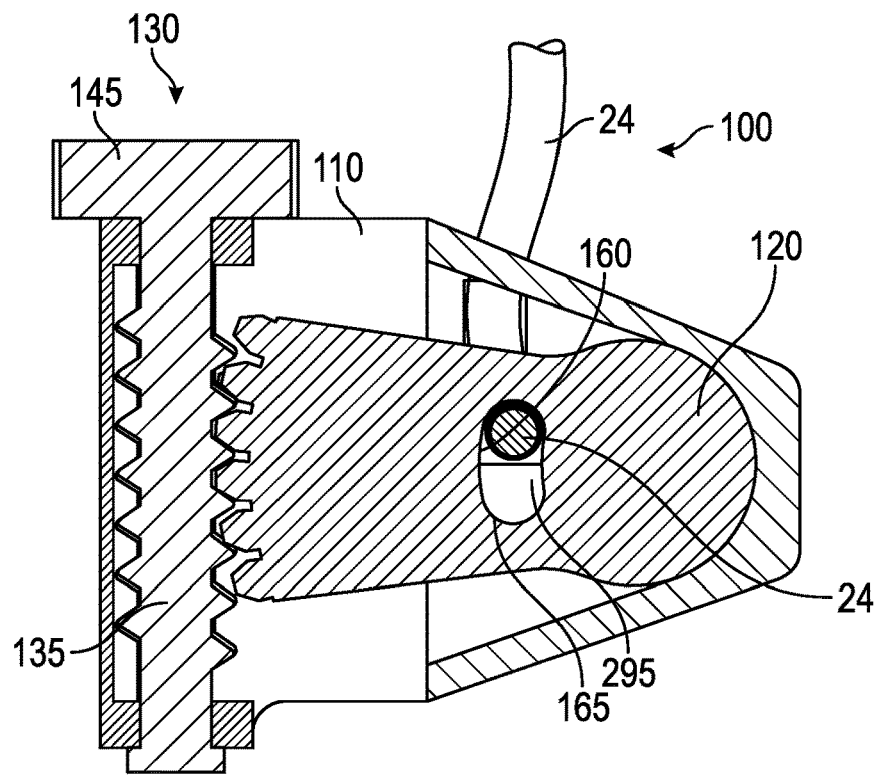
FIG. 7A-7D depict cross-sectional views of a stable flow regulator assembly in varying stages of operation.

FIGS. 7A-7D illustrate one mode of operation of the stable flow regulator assembly 100. In FIG. 7A, the assembly 100 is depicted with the worm wheel 120 in a position within the body 110 where the worm wheel tube slot 165 is aligned with the body tube passage 160. In this position, the tube 24 extends through the tube slot 165 and the tube passage 160 with little or no compression on the tube 24, thereby permitting full flow of fluid through the tube 24.

Figure 7B:
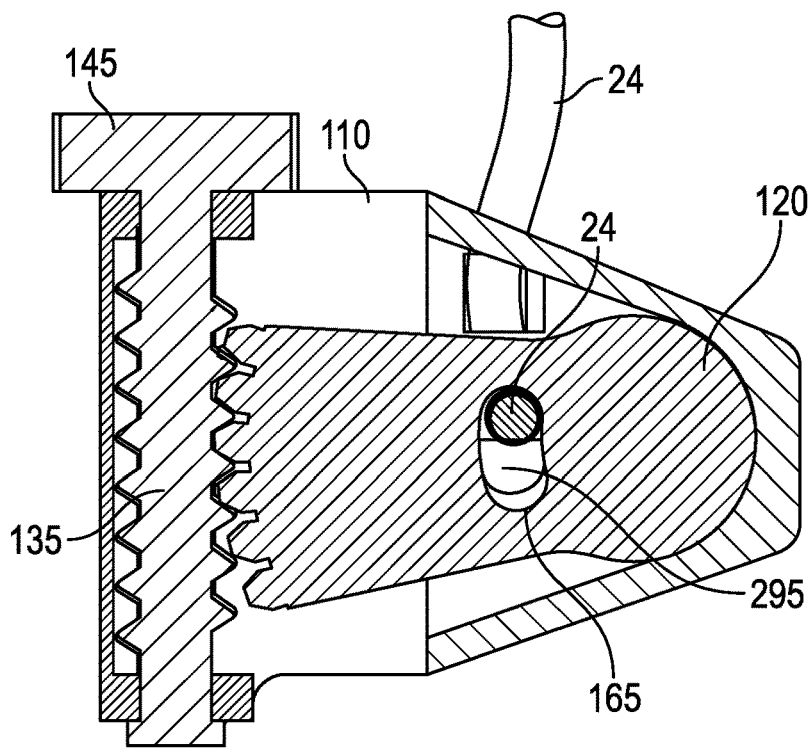

In FIG. 7B, the worm gear dial 145 has rotated, thereby rotating the worm gear thread 135, and causing the worm wheel 120 to rotate or pivot downward. As the worm wheel 120 rotates and the tube slot 165 and tube passage 160 become slightly offset or misaligned, the tube slot 165 presses downwardly against the tube 24, and slightly compresses the tube 24 against the tube passage support 295.

Figure 7C:
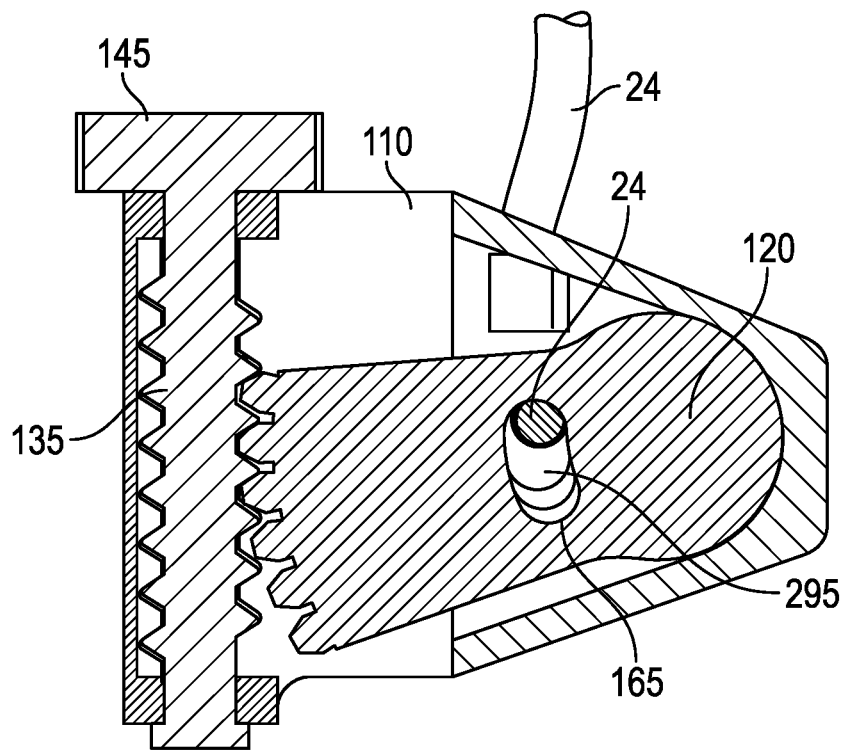

Further rotation of the worm gear dial 145 results in continued rotation downward of the worm wheel 120, as depicted in FIG. 7C. In this orientation, significant compression of the tube 24 is illustrated as the tube slot 165 continues to press the tube 24 further toward the tube passage support 295. The stable flow regulator assembly 100 can be kept in this, or a similar position, with slightly or significantly reduced flow of fluid through the tube 24, caused by the deformation of the tube 24 as it is pressed against the tube passage support 295. The tube 24 can either be opened further by reversing rotation of the worm gear dial 145, or it can be further closed by continuing the rotation of the dial 145 in the same direction depicted as it has progressed through FIGS. 7A-7C. The worm wheel will not rotate or slip on its own without user intervention because rotation or pivoting of the worm wheel 120 will be restricted or prevented by the engaged worm wheel teeth 140 with the worm gear thread 135.

Figure 7D:
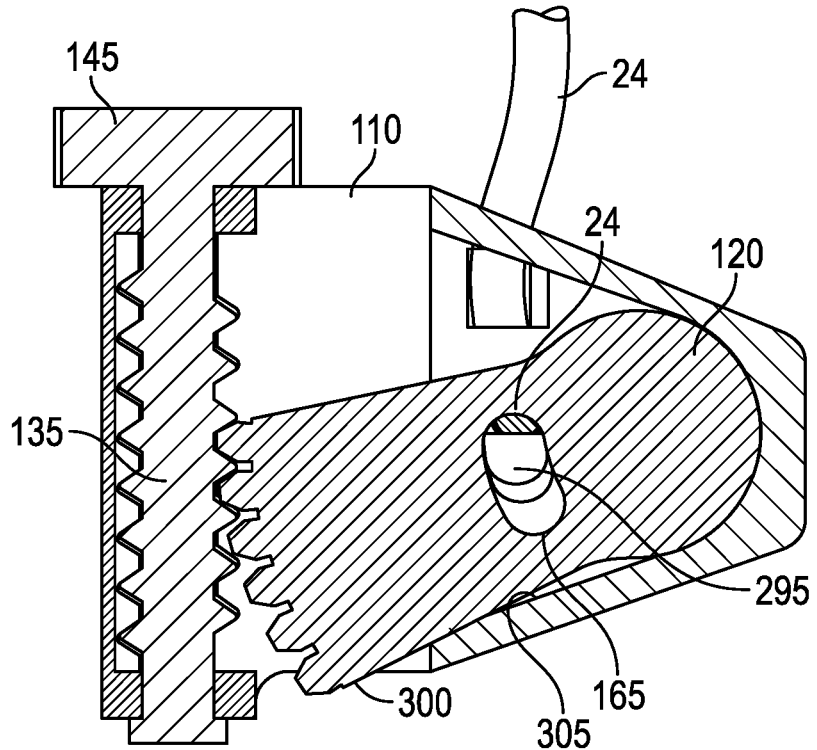

FIG. 7D depicts the tube 24 as completely compressed, thereby completely restricting flow of fluid through the tube 24, as the worm wheel 120 continues to rotate or pivot downwardly. In some embodiments, in order to prevent severing the tube 24 between the tube passage support 295 and the worm wheel tube slot 165, a bottom wall 300 of the worm wheel 120 may be configured to contact or engage an internal wall 305 of the body 110, thereby preventing or restricting further rotation of the worm wheel 120. The tube 24 can be opened by rotating the worm gear dial 145 in the opposite direction than that used to compress the tube 24.

Figure 8:
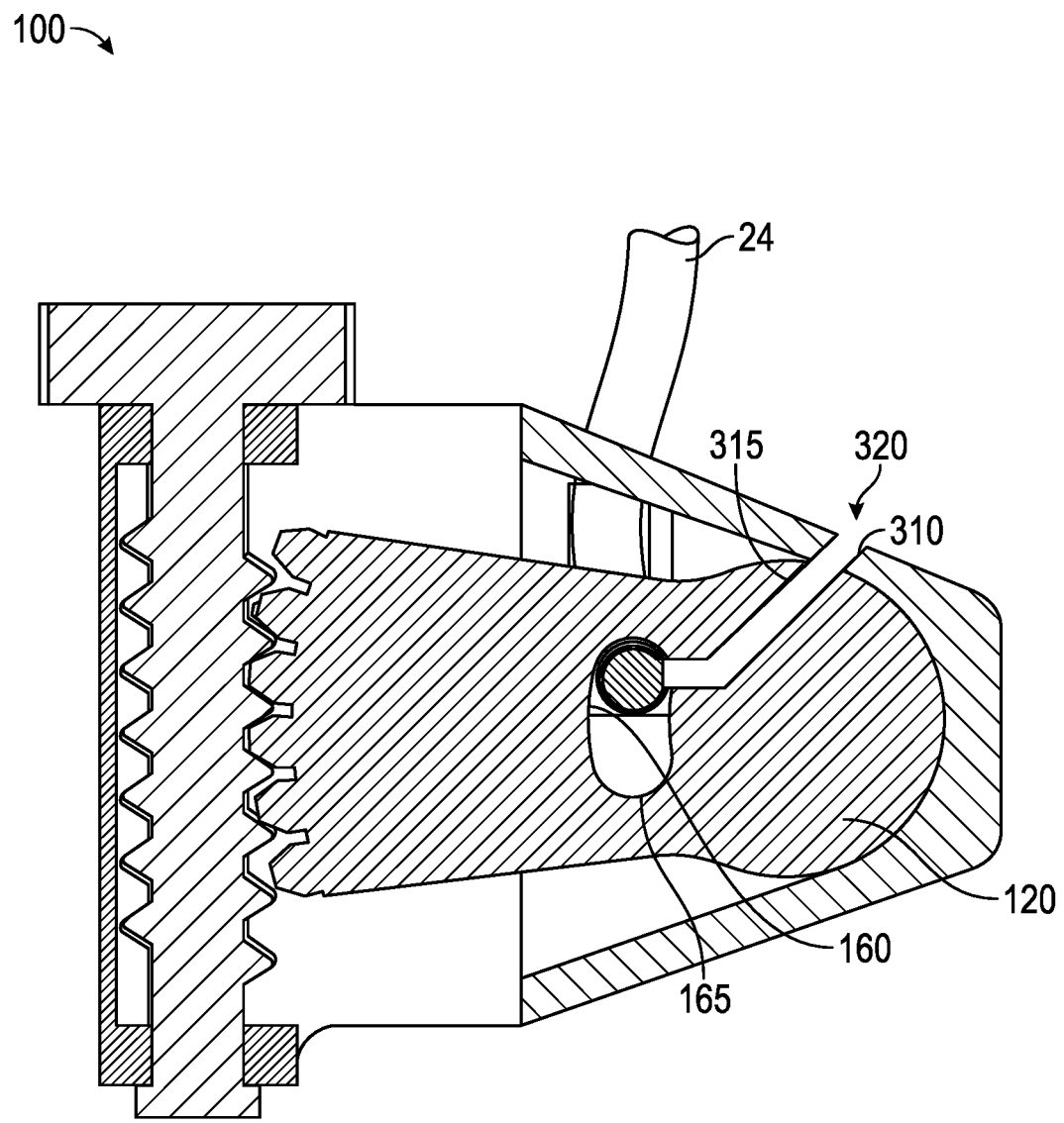
FIG. 8 is a partial cross-sectional view of a stable flow regulator assembly described herein.

In embodiments described above, the stable flow regulator assembly 100 is used by inserting one end of tubing through the body tube passage 160 and the worm wheel tube slot 165 prior to use of the assembly 100. In some embodiments, the assembly 100 can be used in intravenous systems or tubing that is already in use. For example, FIG. 8 illustrated embodiments of an assembly 100 that can be used on a tubing system that is already in use and does not have a free end to extend through the body tube passage 160 and worm wheel tube slot 165. In some embodiments, the assembly 100 can include a body 110 and a worm wheel 120 with slight modifications that permit inserting of the tube 24 into the body tube passage 160 and the worm wheel tube slot 165 without advancing one end of the tube 24 through the passage 160 and slot 165. As illustrated, the body 110 can include a traversing channel 310 that extends from one side of the body 110 to the other side of the body 110. In some embodiments, this traversing channel 310 can be configured to align with a worm wheel channel 315 and form a loading passage 320 that permits the tube 24 to slide through the passage 320 into place extending through the body tube passage 160 and the worm wheel tube slot 165. In these embodiments, the assembly 100 can be added to, or removed from, a tube 24 or tubing system that is in use.

Figure 9:
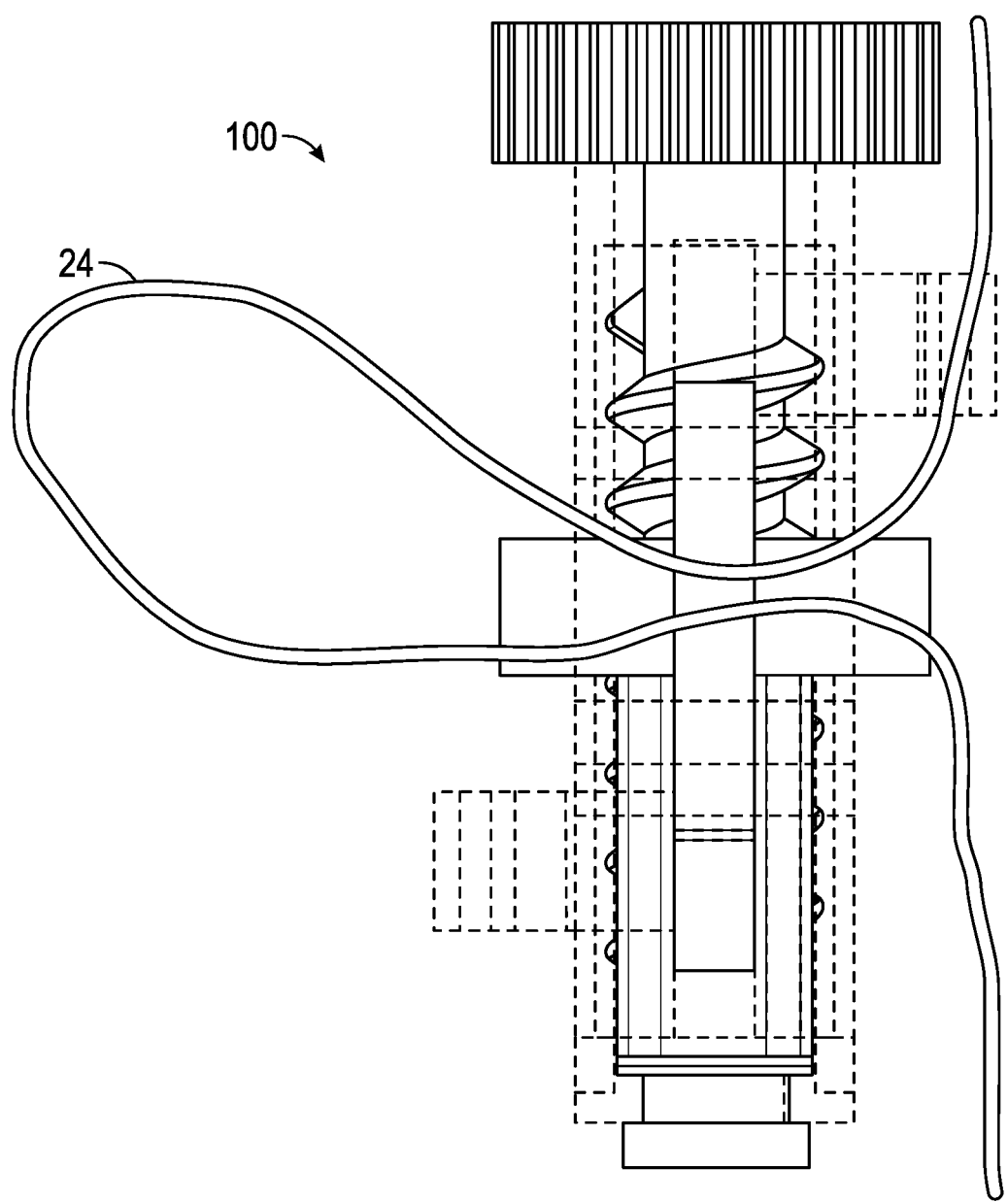
FIG. 9 depicts a partial transparent elevation view of a stable flow regulator assembly described herein.

FIG. 9 illustrates additional embodiments of an assembly 100 that can be used on a tubing system that is already in use and does not have a free end to extend through the body tube passage 160 and worm wheel tube slot 165. In some embodiments, the assembly 100 includes a tube passage 160 and a tube slot 165 that is sized sufficiently to permit insertion therethrough of a doubled tube 24. The tube 24 can be bent back upon itself and inserted through a tube passage and slot 160, 165 having a larger size to permit passage of the tubing therethrough. In these embodiments, the assembly 100 can be used on a tube 24 or tubing system that is already in use.

Figure 10:
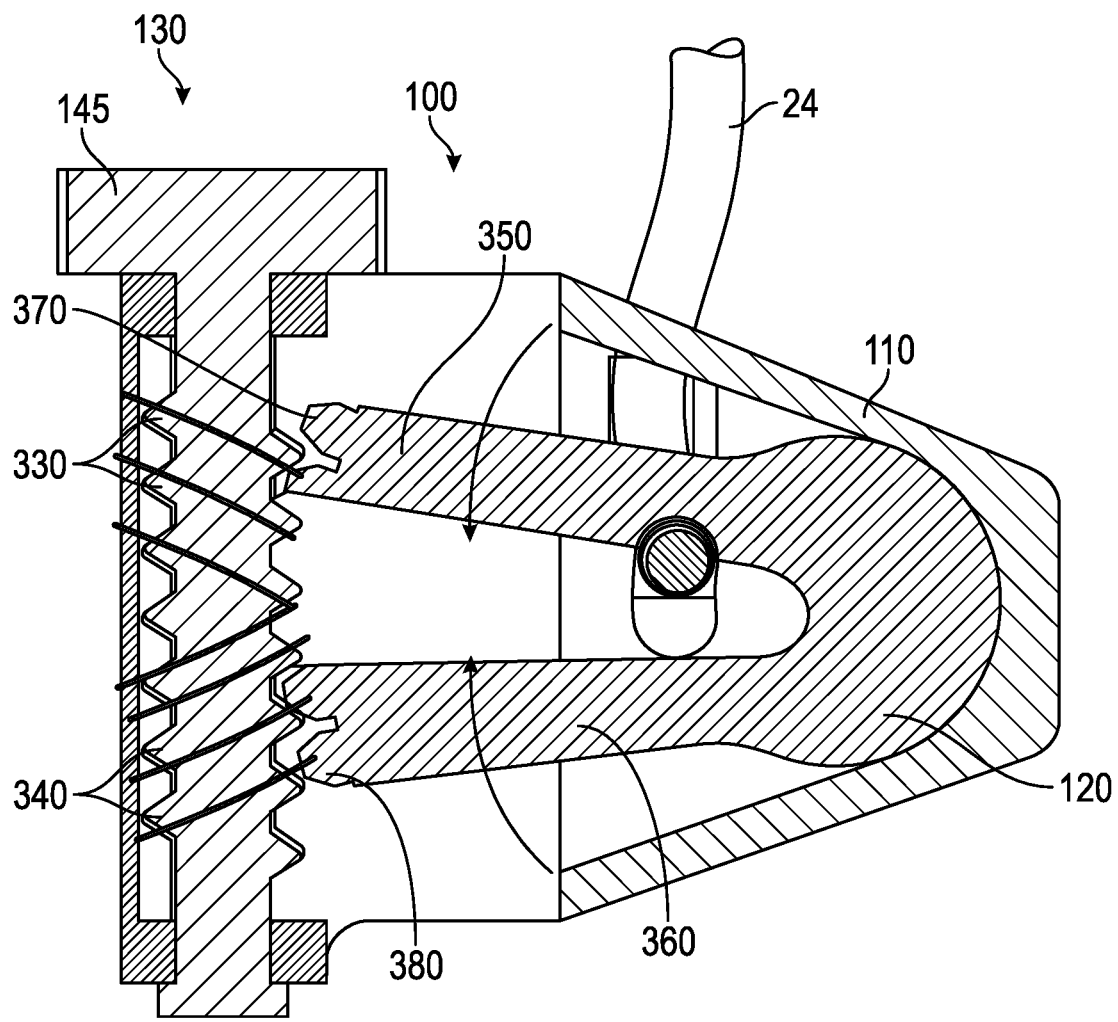
FIG. 10 depicts a partial cross-sectional view of a stable flow regulator assembly described herein.

FIG. 10 illustrates assembly 100 embodiments that provide another operation for clamping down on the tube 24. In these embodiments, the body 110 is similar to other embodiments described above, but the worm wheel 120 and the worm gear 130 have variations from those described in other embodiments. As illustrated, in some embodiments, the worm gear 130 has a first set of worm gear threads 330 and a second set of worm gear threads 340. The first and second sets 330, 340 are separated from each other and have opposite orientations. The worm wheel 120 is configured to reside within the body 110, but in some embodiments, the worm wheel 120 includes a first arm 350 and a second arm 360 that both extend toward the worm gear 130 when assembled. As illustrated, the first and second arms 350, 360 extends toward the worm gear 130 in a slight departing angle, creating a gap between the arms 350, 360. At the end of the arms 350, 360 are a first set of gears or teeth 370 on the first arm 350 and a second set of teeth 380 on the second arm 360. The first set of teeth 370 are configured to engage the first set of worm gear threads 330 on the worm gear 130, and the second set of teeth 380 are configured to engage the second set of worm gear threads 340.

When the worm gear dial 145 is rotated, the worm gear 130 rotates, and the opposing oriented worm gear threads 330, 340 drive the first and second arms 350, 360 to draw towards each other and reduce the angle of departure between the two arms 350, 360. As the arms 350, 360 are drawn toward each other, the tube 24, which is shown as extending between the arms 350, 360, is compressed between the arms 350, 360. Further rotation of the worm gear dial 145 draws the arms 350, 360 closer together and further compresses the tube 24. Rotating the worm gear dial 145 in an opposite direction results in the worm gear threads 330, 340 driving the first and second arms 350, 360 to move away from each other and increase the angle of departure between the two arms 350, 360, which results in less force being applied to the tube 24 and permits more fluid to flow through the tube 24.

Figure 11:
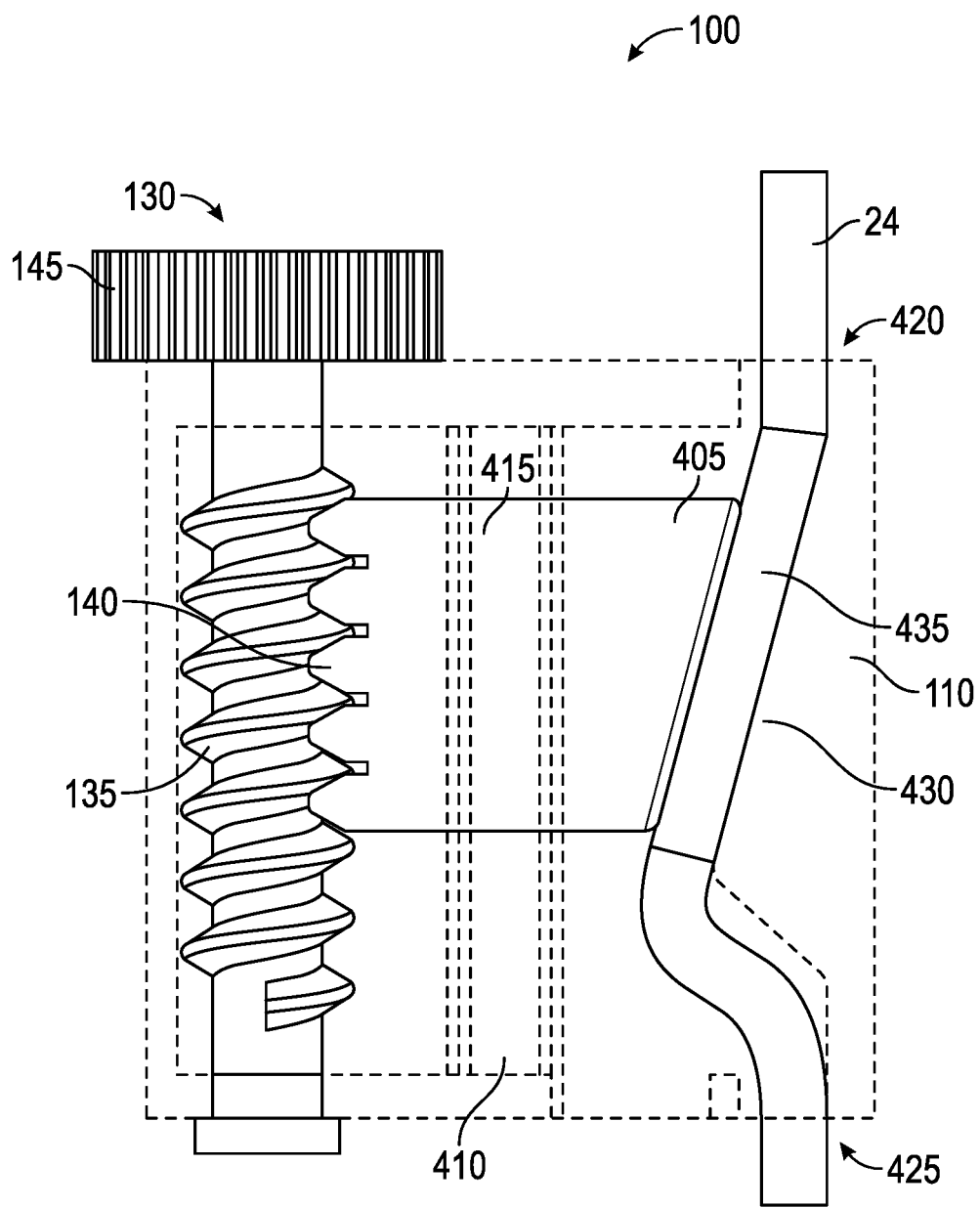
FIG. 11 is a partial transparent elevation view of a stable flow regulator assembly described herein.

FIG. 11 illustrates assembly 100 embodiments that provide another operation for clamping down on the tube 24. In these embodiments, the body 110 is similar to other embodiments described above, and is described with similar reference numeral designations, but in these embodiments, the worm gear 130 operates a rack 405 that is linearly driven within the body 110 along a rack track 410 that extends along the inner surface of the body 110. The rack 405 has a complimentary channel 415 that is configured to ride linearly along the track 410 during operation of the assembly 100. As described with other embodiments, the worm gear 130 includes worm gear threads 135 that engages teeth 140 on the rack 405 to move the rack 405 into a plurality of positions. As the worm gear 130 is rotated, the worm gear threads 135 will also rotate, and the rack teeth 140 engaging the gear threads 135 will move the rack 405 upward and downward, depending on the direction of rotation of the worm gear 130, and the rack 405 will slide linearly within the body 110 as the rack channel 415 slides along the rack track 410.

The body includes an entry opening 420, through which the tube 24 can enter the body, and an exit opening 425, through which the tube 24 can exit the body. The body includes an internal compression portion 430, against which the tube 24, along a compression section 435 of the tube 24, can be compressed between the rack 405 and the body 110.

As depicted in FIG. 11, the compression portion 430 can form a wedge along which the tube 24 rests. During use, as the rack 405 is moved upward and downward within the body 110 by the worm gear 130, the rack 405 will compress or release the tube 24 against the compression portion 430. As the rack 405 moves downward, in the embodiments shown in FIG. 11, the rack 405 will compress the tube 24 along the compression section 435. As it continues to move downward, the rack 405 will compress the compression section 435 to a closed position such that fluid will be completely restricted from flowing through the tube 24. When rotation of the worm gear 130 is reversed, the rack 405 moves upward, and compression of the compression section 435 is released to permit fluid flow through the tube 24. Fluid flow through the tube 24 can be adjusted by rotation of the worm gear 130.

Figure 12:
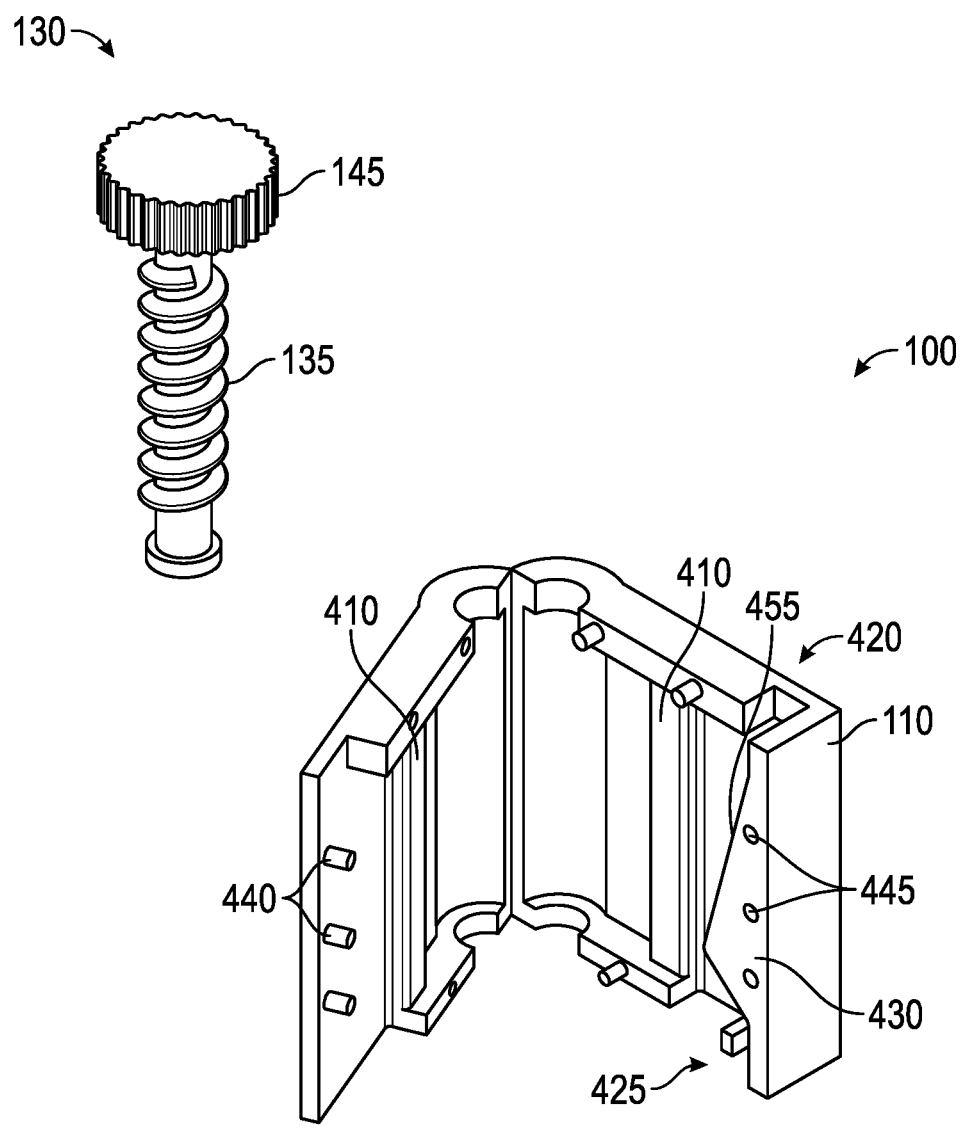
FIG. 12 depicts an exploded view of a stable flow regulator assembly described herein.

FIG. 12 illustrates an exploded view of the assembly 100. As depicted, the worm gear 130 includes a worm gear dial 145 and one or more worm gear threads 135. As described in other embodiments discussed herein, the worm gear is configured to be retained within the body 110 in a similar manner as discussed above. The body 110 can be secured together by snap fit mechanisms, or by an adhesive, ultrasonic bonding, or other manufacturing processes. As depicted in the embodiments of FIG. 12, snap fit protrusions 440 and recesses 445 can be used to secure body 110 together. The body 110 has similar features and functions as described in embodiments described herein.

The rack 405 is illustrated as having the rack channel 415 on both sides of the rack 405. While the embodiments depicted in FIG. 12 show the rack 405 as having the rack channel 415 and the body 405 as having the rack tracks 410, in some embodiments, the channel 415 may be positioned on the body 405, and the channel 415 may be positioned on the rack 405. The rack 405 includes a compression surface 450 that is at an angle askew from the normal planes of the rack 405. In FIG. 12, the compression portion 430 includes a complementary pressing surface 455 that is preferably askew from normal planes at the same angle as the compression surface 450. In some embodiments, when the rack 405 is received within the body 110, and the tracks 410 are received in the channels 415, such that the rack 405 can move linearly along the tracks 410, the compression surface 450 of the rack 405 is generally parallel with the pressing surface 455 of the body 110. The configuration creates a generally flat pressing surface against the tube 24 when the rack 405 moves against the compression portion 430.

While FIG. 12 depicts the compression surface 450 and pressing surface 455 as generally planar structures that as aligned at an angle askew from normal places of the rack 405 or body 110, the surfaces 450, 455 can have varying shapes or profiles. For example, in some embodiments, not shown, the compression surface 450 can have a convex, or bulbous, shape, and the pressing surface 455 can have a complementary concave surface, such that the convex compression surface 450 is configured to fit against the concave pressing surface 455. Other complementary profiles can also be used to provide a closing force on the tube 24. As described, the surfaces 450, 455 convert the linearly moving rack 405 to an angulated pressing force that can gradually move together to pinch or close the tube 24 between the surfaces 450, 455. Additionally, the angulated arrangement creates two directional components of force when the rack 405 is pressed against the pressing surface 455, one in the linearly vertical direction and another normal force against the worm screw. These two components of force help keep the teeth 140 pressed against the worm gear thread 135, which functions to restrict movement of the rack 405 after the position is set for the rack 405 within the body 110.

FIGS. 13A-13D illustrate modes of operation of the stable flow regulator assembly 100 according to some embodiments. In FIG. 13A, the assembly 100 is depicted with the worm gear 130 positioned rotationally within the body 110. The worm gear thread 135 engages the rack 405 teeth 140 to hold the rack 405 in an upward position such that the tube 24 extends through the body 110. The rack 405 is positioned relative to the compression portion 430 such that the tube 24 is not compressed, and free flow is permitted through the tube 24.

In FIG. 13B, the worm gear 130 has rotated, causing rotation of the worm gear thread 135, and causing teeth 140 on the rack 405 to drive the rack 405 downward. As the rack 405 is driven downward, the rack 405 draws closer to the compression portion 430, and the rack 405 presses against the tube 24 that extends between the rack 405 and the compression portion 430. As the rack 405 presses against the tube 24, the rack 405 slightly compresses the tube 24 against the compression portion 430.

As the worm gear 130 is further rotated, the rack 405 continues downwardly within the body 110, as depicted in FIG. 13C. In this configuration, significant compression of the tube 24 is illustrated as the rack 405 is moved closer to the compression portion 430. The stable flow regulator assembly 100 can be kept in this, or a similar position, with slightly or significantly reduced flow of fluid through the tube 24, caused by the deformation of the tube 24 as it is compressed between the rack 405 and the compression portion 430. The tube 24 can either be opened further by reversing rotation of the worm gear 130, or it can be further closed by continuing the rotation in the same direction depicted as it has progressed through FIGS. 13A-13C. As described previously, the rack 405 will not move upwardly or slip on its own without user intervention because movement of the rack 405 is restricted or prevented by the engaged teeth 140 of the rack 405 with the worm gear thread 135.

FIG. 13D depicts the tube 24 as completely compressed, thereby completely restricting flow of fluid through the tube 24, as the rack 405 continues to descend in the body 110. As described with some embodiments, in order to prevent severing the tube 24 between the rack 405 and the compression portion 430, the body 110 may include a bottom wall that operates to restrict movement of the rack 405 too far down in the body 110. The tube 24 can be opened, thereby permitting fluid to begin flowing through the tube 24, by rotating the worm gear 130 in the opposite direction than that used to compress the tube 24.

Described herein are embodiments that include, but are not limited to, the following clauses:

Clause 1. A stable flow regulator assembly comprising:
a body comprising:
a first side configured to be coupled to a second side;
the first and second sides each comprising respective first and second apertures, the apertures configured to be aligned when the first side is coupled to the second side;
a first and second gear mount aligned on an axis; and
a worm gear comprising a gear thread and configured to be rotationally positioned through the first and second gear mount along the axis; and
a worm wheel comprising a rotation axis, worm wheel teeth spaced from the rotation axis, and a tube slot, the worm wheel being configured to be rotationally held within the body, the worm wheel teeth being configured to engage the gear thread, and the tube slot being configured to align with the first and second apertures,
wherein rotation of the worm gear translates to rotation of the worm wheel and moves the tube slot relative to the first and second apertures.

Clause 2. The stable flow regulator assembly of clause 1, wherein the tube slot and the first and second apertures are each configured to receive a tube therethrough.

Clause 3. The stable flow regulator assembly of clause 2, wherein when the tube slot is moved relative to the first and second apertures, the tube slot is configured to compress the tube.

Clause 4. The stable flow regulator assembly of clause 3, wherein when the worm gear is rotated in an opposite direction, the tube slot moves toward alignment with the first and second apertures and releases compressive forces on the tube.

Clause 5. The stable flow regulator assembly of clause 1, wherein the worm wheel comprises opposingly extending shafts that are received by the first and second sides of the body and about which the worm wheel pivots.

Clause 6. The stable flow regulator assembly of clause 1, wherein the body comprises a planar surface along an interior surface of the first and second apertures, and wherein the tube slot is configured to press the tube against the planar surface when the worm wheel moves in a first, closing direction.

Clause 7. The stable flow regulator assembly of clause 1, wherein the body and the worm wheel are configured to receive the tube without extending an end of the tube through the first and second apertures and the tube slot.

Clause 8. The stable flow regulator assembly of clause 7, wherein the body comprises a first channel and the worm wheel comprises a second channel, and the first and second channels align to form a loading passage.

Clause 9. The stable flow regulator assembly of clause 7, wherein the first and second apertures and the tube slot are sized to receive therethrough the tube folded upon itself.

Clause 10. A flow regulator assembly comprising:
a body comprising an enclosed housing having an aperture extending through the body;
a worm gear comprising a gear thread and configured to be rotationally positioned through the body; and
a worm wheel configured to be rotationally positioned within the enclosed housing and to be moved rotationally by rotation of the worm gear, the worm wheel comprising a tube slot configured to align with the aperture,
wherein rotation of the worm gear translates to rotation of the worm wheel within the body and moves the tube slot relative to the first and second apertures.

Clause 11. The flow regulator assembly of clause 10, wherein the tube slot and the aperture are each configured to receive a tube therethrough.

Clause 12. The flow regulator assembly of clause 11, wherein when the tube slot is moved relative to the aperture, the tube slot is configured to compress a tube extending through the aperture.

Clause 13. The flow regulator assembly of clause 10, wherein the body comprises a planar surface along an interior surface of the aperture, and wherein the tube slot is configured to press the tube against the planar surface when the worm wheel moves in a first, closing direction.

Clause 14. The flow regulator assembly of clause 10, wherein the body and the worm wheel are configured to receive the tube without extending an end of the tube through the first and second apertures and the tube slot.

Clause 15. The flow regulator assembly of clause 14, wherein the body comprises a first channel and the worm wheel comprises a second channel, and the first and second channels align to form a loading passage.

Clause 16. The stable flow regulator assembly of clause 14, wherein the first and second apertures and the tube slot are sized to receive therethrough the tube folded upon itself.

Clause 17. A stable flow regulator assembly comprising:
a body comprising an enclosed housing having an aperture extending through the body;
a worm gear comprising a first gear thread and a second gear thread extending in a opposite direction as the first gear thread, the worm gear being configured to be rotationally positioned within the enclosed housing; and
a worm wheel comprising a first arm and a second arm, the first arm being configured to engage the first gear thread, and the second arm being configured to engage the second gear thread, the worm wheel further comprising a tube slot configured to align with the aperture,
wherein rotation of the worm gear in a first direction moves the first and second arm toward each other.

Clause 18. The stable flow regulator assembly of clause 17, wherein the tube slot and the aperture are each configured to receive a tube therethrough.

Clause 19. The stable flow regulator assembly of clause 18, wherein when the first and second arms move toward each other, the first and second arms are configured to compress a tube extending through the aperture.

Clause 20. The stable flow regulator assembly of clause 18, wherein rotation of the worm gear in a second direction, opposite the first direction, moves the first and second arms aways from each other.

Clause 21. A stable flow regulator assembly for regulating fluid flow, comprising:
a body comprising:
a first side configured to be coupled to a second side;
a first and second gear mount aligned on an axis between the first side and second side;
a tube pathway configured to receive and retain a tube extending through the body;
a worm gear comprising a gear thread and configured to be rotationally positioned through the first and second gear mount along the axis; and
an actuator configured to be positioned within, and moveable relative to, the body, the actuator comprising teeth configured to engage the gear thread,
wherein rotation of the worm gear translates to movement of the actuator within the body to move the actuator from an open configuration, wherein the regulator permits fluid flow, to a closed configuration, wherein the regulator restricts fluid flow.

Clause 22. The stable flow regulator assembly of clause 21, wherein the first and second sides each comprise respective first and second apertures, the apertures configured to be aligned when the first side is coupled to the second side, wherein the actuator comprises a worm wheel comprising a rotation axis, teeth spaced from the rotation axis, and a tube slot, the worm wheel being configured to be rotationally held within the body, the teeth being configured to engage the gear thread, and the tube slot being configured to align with the first and second apertures, wherein rotation of the worm gear translates to rotation of the worm wheel and moves the tube slot relative to the first and second apertures.

Clause 23. The stable flow regulator assembly of clause 21, wherein the actuator comprises a rack configured to be movable along a linear track within the body.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure, element or feature relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A stable flow regulator assembly for regulating fluid flow, comprising:
    a body comprising:
    a first side configured to be coupled to a second side;
    a first and second gear mount aligned on an axis between the first side and second side;
    a tube pathway configured to receive and retain a tube extending through the body;
    a worm gear comprising a gear thread and configured to be rotationally positioned through the first and second gear mount along the axis; and
    an actuator configured to be positioned within, and moveable relative to, the body, the actuator comprising teeth configured to engage the gear thread and a tube slot,
    wherein the body and the actuator are configured to receive the tube without extending an end of the tube through the tube pathway and the tube slot, and rotation of the worm gear translates to movement of the actuator within the body to move the actuator from an open configuration, wherein the regulator permits fluid flow, to a closed configuration, wherein the regulator restricts fluid flow.

2. The stable flow regulator assembly of claim 1, wherein the first and second sides each comprise respective first and second apertures, the apertures configured to be aligned when the first side is coupled to the second side, wherein the actuator comprises a worm wheel comprising a rotation axis, the teeth spaced from the rotation axis, and the tube slot, the worm wheel being configured to be rotationally held within the body, the teeth being configured to engage the gear thread, and the tube slot being configured to align with the first and second apertures, wherein rotation of the worm gear translates to rotation of the worm wheel and moves the tube slot relative to the first and second apertures.

3. The stable flow regulator assembly of claim 1, wherein an interface between the actuator and the body is configured to compress the tube when the actuator is in the closed configuration.

4. A stable flow regulator assembly comprising:
    a body comprising:
    a first side configured to be coupled to a second side;
    the first and second sides each comprising respective first and second apertures, the apertures configured to be aligned when the first side is coupled to the second side;
    a first and second gear mount aligned on an axis;
    a worm gear comprising a gear thread and configured to be rotationally positioned through the first and second gear mount along the axis; and
    a worm wheel comprising a rotation axis, worm wheel teeth spaced from the rotation axis, and a tube slot, the worm wheel being configured to be rotationally held within the body, the worm wheel teeth being configured to engage the gear thread, and the tube slot being configured to align with the first and second apertures, wherein the body and the worm wheel are configured to receive a tube without extending an end of the tube through the first and second apertures and the tube slot,
    wherein rotation of the worm gear translates to rotation of the worm wheel and moves the tube slot relative to the first and second apertures.

5. The stable flow regulator assembly of claim 4, wherein the tube slot and the first and second apertures are each configured to receive a tube therethrough.

6. The stable flow regulator assembly of claim 5, wherein when the tube slot is moved relative to the first and second apertures, the tube slot is configured to compress the tube.

7. The stable flow regulator assembly of claim 6, wherein when the worm gear is rotated in an opposite direction, the tube slot moves toward alignment with the first and second apertures and releases compressive forces on the tube.

8. The stable flow regulator assembly of claim 4, wherein the worm wheel comprises opposingly extending shafts that are received by the first and second sides of the body and about which the worm wheel pivots.

9. The stable flow regulator assembly of claim 4, wherein the body comprises a planar surface along an interior surface of the first and second apertures, and wherein the tube slot is configured to press the tube against the planar surface when the worm wheel moves in a first, closing direction.

10. The stable flow regulator assembly of claim 4, wherein the body comprises a first channel and the worm wheel comprises a second channel, and the first and second channels align to form a loading passage.

11. The stable flow regulator assembly of claim 4, wherein the first and second apertures and the tube slot are sized to receive therethrough the tube folded upon itself.

12. The stable flow regulator assembly of claim 4, wherein an interface between the worm wheel and the body is configured to compress the tube when the worm wheel is rotated within the body.

13. A flow regulator assembly comprising:
a body comprising an enclosed housing having an aperture extending through the body;
a worm gear comprising a gear thread and configured to be rotationally positioned through the body; and
a worm wheel configured to be rotationally positioned within the enclosed housing and to be moved rotationally by rotation of the worm gear, the worm wheel comprising a tube slot configured to align with the aperture,
wherein the body and the worm wheel are configured to receive a tube without extending an end of the tube through the aperture and the tube slot, and rotation of the worm gear translates to rotation of the worm wheel within the body and moves the tube slot relative to the aperture.

14. The flow regulator assembly of claim 13, wherein the tube slot and the aperture are each configured to receive a tube therethrough.

15. The flow regulator assembly of claim 14, wherein when the tube slot is moved relative to the aperture, the tube slot is configured to compress a tube extending through the aperture.

16. The flow regulator assembly of claim 13, wherein the body comprises a planar surface along an interior surface of the aperture, and wherein the tube slot is configured to press the tube against the planar surface when the worm wheel moves in a first, closing direction.

17. The flow regulator assembly of claim 13, wherein the body comprises a first channel and the worm wheel comprises a second channel, and the first and second channels align to form a loading passage.

18. The flow regulator assembly of claim 13, wherein the aperture and the tube slot are sized to receive therethrough the tube folded upon itself.

* * * * *